United States Patent [19]

Shoji et al.

[11] Patent Number: 4,727,185
[45] Date of Patent: Feb. 23, 1988

[54] PROCESS FOR PREPARATION OF 3,3',4,4'-BIPHENYLTETRACARBOXYLIC ACID SALTS

[75] Inventors: Fusaji Shoji; Fumio Kataoka, both of Yokohama, Japan

[73] Assignee: Hitachi, Ltd., Japan

[21] Appl. No.: 820,629

[22] Filed: Jan. 21, 1986

[30] Foreign Application Priority Data

Jan. 21, 1985 [JP] Japan ................................. 60-7535

[51] Int. Cl.$^4$ ............................................ C07C 51/347
[52] U.S. Cl. ...................... 562/481; 502/172; 502/185; 502/223; 502/306; 502/313; 502/326; 502/327; 502/328; 560/96; 562/488
[58] Field of Search ................... 562/481, 488; 560/96

[56] References Cited

U.S. PATENT DOCUMENTS

| 2,823,230 | 2/1958 | Raecke | 562/481 |
| 2,906,774 | 9/1959 | Raecke et al. | 560/481 |
| 3,751,456 | 8/1973 | Wu | 562/488 |

*Primary Examiner*—Werren B. Lone
*Assistant Examiner*—Vera C. Clarke
*Attorney, Agent, or Firm*—Antonelli, Terry & Wands

[57] ABSTRACT

When a 4-halogenoorthophthalic acid salt is dissolved together with a base in an alkaline aqueous solution and the solution is heated in the presence of a catalyst comprising a noble metal supported on a carrier, a formic acid salt and a small amount of an aliphatic compound containing a hydroxyl group, a 3,3',4,4'-biphenyltetracarboxylic acid salt is obtained in a high yield.

4 Claims, No Drawings

PROCESS FOR PREPARATION OF 3,3',4,4'-BIPHENYLTETRACARBOXYLIC ACID SALTS

BACKGROUND OF THE INVENTION (1) Field of the Invention

The present invention relates to a process for the preparation of a 3,3', 4,4'-biphenyltetracarboxylic acid salt by dehalogenodimerization of a 4-halogenoorthophthalic acid salt.

(2) Description of the Prior Art

As the conventional process for the preparation of 3,3', 4,4'-biphenyltetracarboxylic acid, there is known a process in which an aqueous solution in which a 4-halogenoorthophthalic acid salt and an alkali metal hydroxide are dissolved is heated at 50 to 150° C. in the presence of a catalyst having metallic palladium supported on a carrier and a small amount of methanol and the reaction is conducted for 0.2 to 30 hours (see Japanese Patent Application Laid-Open Specification No. 20705/80). In this dehalogenodimerization reaction, however, the yield is not high. That is, the yield is about 29% to about 58.6%. 3,3', 4,4'-Biphenyltetracarboxylic dianhydride prepared from this 3,3', 4,4'-biphenyltetracarboxylic acid salt can be used as a starting material of a polyimide or an epoxy-curing agent. From the industrial viewpoint, in order for this salt to be used as the starting material of various polymers, it is desirable that the salt be obtained in a high yield, for example, a yield of at least 80%. If the yield is low, the cost of the starting material of a polyimide which is a heat-resistant resin is increased.

SUMMARY OF THE INVENTION

It is a primary object of the present invention to provide a process for the dehalogenodimerization of a 4-halogenoorthophthalic acid salt, in which 3,3', 4,4'-biphenyltetracarboxylic acid salt can be prepared in a high yield and be recovered very easily.

In accordance with the present invention, there is provided a process for the preparation of a 3,3', 4,4'-biphenyltetracarboxylic acid salt by the dehalogenodimerization of a 4-halogenoorthophthalic acid salt, which comprises heating and reacting an alkaline aqueous solution containing, dissolved therein, a 4-halogenoorthophthalic acid salt and a base in the presence of (1) a catalyst comprising a noble metal supported on a carrier, a formic acid salt and a small amount of an aliphatic compound containing a hydroxyl group or (2) a catalyst comprising a noble metal supported on a carrier, which has been treated with an aliphatic compound containing a hydroxyl group in advance, and a formic acid salt. According to this process, a 3,3', 4,4'-biphenyltetracarboxylic acid salt can be obtained in a high yield and recovery of the salt can be performed very easily.

DETAILED DESCRIPTION OF THE PREFERRED EMBODIMENTS

As the 4-halogenoorthophthalic acid salt that is used in the present invention, there can be mentioned, for example, alkali metal salts, such as sodium, potassium and lithium salts, of 4-chloroorthophthalic acid, 4-bromoorthophthalic acid and 4-iodoorthophthalic acid, and sodium and potassium salts of 4-bromoorthophthalic acid and 4-chloroorthophthalic acid are preferred. In order to obtain the intended salt in a high yield, it is especially preferred that sodium and potassium salts of 4-bromoorthophthalic acid be used.

As the process for the preparation of chlorinated orthophthalic acid salts and brominated orthophthalic acid salts to be used mainly for the preparation of 4-halogenoorthophthalic acid salts such as 4-chloroorthophthalic acid salts and 4-bromoorthophthalic acid salts, there can be mentioned known processes disclosed, for example, in Ayling, J. Chem. Soc., 1929, 253, Japanese Patent Application Laid-Open Specification No. 45438/81, British Patent No. 628,401 and Hans Waldmon, J. Prakt. Chem., 126, 65–68, 1930. According to these known processes, there is obtained a halogenated orthophthalic acid salt mixture containing not only a 4-halogenoorthophthalic acid salt but also a 3-halogenoorthophthalic acid salt, a 3,4-dihalogenoorthophthalic acid salt, a 4,5-dihalogenoorthophthalic acid salt and unreacted orthophthalic acid salt.

According to the process of the present invention, even if the above-mentioned halogenated orthophthalic acid salt mixture is used, the 3,3 ', 4,4'-biphenyltetracarboxylic acid salt can be obtained in a high yield as the dehalogenodimerization reaction product, and formation of the 2,3,3 ', 4'-biphenyltetracarboxylic acid is controlled to a level much lower than the expected level. Accordingly, not only a 4-halogenophthalic acid salt alone but also a halogenated orthophthalic acid mixture can be used in the dehalogenodimerization reaction of the 4-halogenoorthophthalic acid salt according to the present invention.

As the base used in the present invention, there can be mentioned alkali metal hydroxides such as potassium hydroxide, sodium hydroxide and lithium hydroxide, alkaline earth metal hydroxides such as calcium hydroxide, carbonates such as potassium carbonate, bicarbonates such as potassium bicarbonate, and alkoxides such as potassium methoxide. As another base, there can be mentioned tetra-lower-alkyl (1 to 3 carbon atoms)-ammonium hydroxides such as tetramethylammonium hydroxide and tetraethylammonium hydroxide. Potassium hydroxide, sodium hydroxide and potassium carbonate are especially preferred. The base is used in the form of an aqueous solution. It is preferred that amount of the base used be such that the pH value of the aqueous solution containing the base and halogenated orthophthalic acid salt, dissolved therein, be more than 7, especially at least 10. More specifically, it is preferred that the base be used in an amount of at least 1.0 mole, especially 1.5 to 5.0 moles, per mole of the above-mentioned halogenated orthophthalic acid salt mixture (monosodium salts of orthophthalic acid and halogenoorthophthalic acids). If the amount of the base used is smaller than 1.0 mole per mole of the halogenated orthophthalic acid salt mixture, the yield of the intended 3,3 ', 4,4'-biphenyltetracarboxylic acid salt is low and the reaction is not completed. In contrast, if the amount of the base used is larger than 5.0 moles per mole of the halogenated orthophthalic acid salt mixture, side reactions such as formation of a phthalic acid salt by dehalogenation are caused to occur and the yield is reduced.

As the catalyst comprising a noble metal supported on a carrier, that is used in the present invention, there can be mentioned catalysts comprising Pd supported on a carrier, such as a palladium (Pd)-active carbon, Pd-alumina, Pd-calcium carbonate and Pd-barium sulfate. A Pd-active carbon catalyst is especially preferred. It is preferred that the Pd content in the catalyst comprising Pd supported on a carrier be 1.0 to 10% by weight, especially 2.0 to 8.0% by weight.

Furthermore, there can be used platinum (Pt)-carbon, Pt-alumina, ruthenium (Ru)-carbon, Ru-alumina, rhodium (Rh)-carbon and Rh-alumina. In these noble metal-supported catalysts, it is preferred that the content of Pt, Ru or Rh be 1.0 to 10% by weight.

In the present invention, the amount of the catalyst used comprising a noble metal supported thereon is changed according to the kind of the catalyst, the reaction temperature, the reaction time and other conditions, but ordinarily, the amount of the catalyst is 0.005 to 5% by weight, especially about 0.01 to about 2% by weight, as calculated as the noble metal based on the halogenated orthophthalic acid salt. If the amount of the catalyst is smaller than 0.005% by weight, the reaction is not sufficiently advanced and the yield is low. The amount of the catalyst may be larger than 5% by weight, but in this case, the cost of the product is increased.

Various aliphatic compounds having a hydroxyl group can be used in combination with the above-mentioned catalyst or for treating the above-mentioned catalyst in advance. For example, there can be mentioned methyl alcohol, ethyl alcohol, propyl alcohol, butyl alcohol, amyl alcohol, ethylene glycol, ethylene glycol monomethyl ether and ethylene glycol monoethyl ether. It is preferred that the amount of the hydroxyl group-containing aliphatic compound used be at least 0.1 mole, especially 0.5 to 20 moles, particularly especially about 1 to about 10 moles, per mole of the above-mentioned halogenated orthophthalic acid salt or the above-mentioned halogenated orthophthalic acid salt mixture. If the amount of the hydroxyl group-containing aliphatic compound is larger than 20 moles per mole of the above-mentioned salt or salt mixture, the yield of the 3,3'-4,4'-biphenyltetracarboxylic acid salt is reduced. Accordingly, use of the hydroxyl group-containing aliphatic compound in such a large amount is not preferred.

As the formic acid salt that is used in the present invention, there can be mentioned alkali metal salts such as sodium formate and potassium formate, and ammonium formate, trimethylammonium formate and triethylammonium formate. This formic acid salt is a catalyst excellent as a hydrogen donor in the dehalogenodimerization reaction of the 4-halogenoorthophthalic acid salt. It is preferred that the amount of the formic acid salt used be 1.0 to 5.0 moles per mole of the 4-halogenoorthophthalic acid salt.

The dehalogenodimerization of the 4-halogenoorthophthalic acid salt is carried out at a reaction temperature of 70 to 150° C., preferably 90 to 120° C. If the reaction temperature is lower than 70° C., the reaction speed is low and a long time is required for completion of the reaction, and therefore, the reaction efficiency is low. If the reaction temperature is higher than 150° C., the yield of the intended 3,3', 4,4'-biphenyltetracarboxylic acid salt is reduced because of occurrence of side reactions. The reaction time depends on the amounts of the noble metal-supported catalyst, the base, the formic acid salt and the hydroxyl group-containing aliphatic compound and the reaction temperature, but the reaction time is ordinarily 1 to 20 hours and preferably 3 to 10 hours.

For example, water is preferably used as the solvent for the dehalogenodimerization of the 4-halogenoorthophthalic acid salt.

The reaction may be carried out under atmospheric pressure. However, in case of the dechlorodimerization of a 4-chloroorthophthalic acid salt, since the reaction speed is low, the yield is increased if the reaction is carried out under an elevated pressure of up to 10 kg/cm$^2$, preferably up to 5 kg/cm$^2$.

EXAMPLES OF THE INVENTION

The present invention will now be described in detail with reference to the following examples. Of course, the scope of the invention is not limited by the following examples.

Example 1

A four-necked flask provided with a thermometer, a reflux cooling tube and a stirrer and having a capacity of 300 ml was charged with 27.5 g of a light yellow powder comprising 80.9% of sodium 4-bromoorthophthalate, 0.9 mole % of sodium 3-bromoorthophthalate and 18.2 mole % of sodium orthophthalate, 13.2 g of 85% potassium hydroxide and 60 g of water, and an aqueous solution was formed. Then, 6.8 g of sodium formate, 4.6 ml of ethanol and 2 g of a metallic palladium (Pd)-carbon catalyst (having a Pd content of 5% by weight and a water content of 50% by weight) were added to the solution and the mixture was stirred at 95 to 100° C. for 6 hours under atmospheric pressure to effect debromodimerization. For determining the yield, after completion of the reaction, the Pd-C catalyst was removed by filtration and the filtrate was made acidic (pH of 1 to 3) by addition of hydrochloric acid, whereby 3,3', 4,4'-biphenyltetracarboxylic acid was formed as a white precipitate. It was found that the yield was 13.1 g (95.2%).

Examples 2 through 4

Procedures of Example 1 were repeated in the same manner except that 13.6 g, 20.4 g or 27.2 g of sodium formate was added to the light yellow powder having a sodium 4-bromoorthophthalate content of 80.9 mole %, potassium hydroxide, water, ethanol and Pd-C (having a Pd content of 5% by weight and a water content of 50% by weight), used in Example 1. Such a high yield as 13.2 g (95.9%), 12.9 g (93.7%) or 12.5 g (90.8%) as 3,3', 4,4'-biphenyltetracarboxylic acid was obtained.

Examples 5 through 7

Procedures of Example 1 were repeated in the same manner except that to the light yellow powder having a sodium 4-bromoorthophthalate content of 80.9 mole %, potassium hydroxide, water, sodium formate and Pd-C (having a Pd content of 5% by weight and a water content of 50% by weight), used in Example 1, was added methanol, n-propyl alcohol, n-butyl alcohol or n-amyl alcohol in an amount of 0.1 mole. Such a high yield as 13.4 g (97.4%), 12.3 g (89.4%) or 12.1 g (87.9%) as 3,3', 4,4'-biphenyltetracarboxylic acid was obtained.

Examples 8 through 10

Procedures of Example 1 were repeated in the same manner except that a Pd-C catalyst having a Pd content of 2% by weight, 7.5% by weight or 10% by weight was added to the light yellow powder having a sodium 4-bromoorthophthalate content of 80.9 mole %, potassium hydroxide, water, ethanol and sodium formate, used in Example 1. Such a high yield as 13.0 g (94.4%), 13.1 g (95.2%) or 12.8 g (93.0%) as 3,3', 4,4'-biphenyltetracarboxylic acid was obtained.

Examples 11 through 14

Procedures of Example 1 were repeated in the same manner except that in the light yellow powder having a sodium 4-bromoorthophthalate content of 80.9 mole %, water, potassium hydroxide, ethanol, sodium formate and the Pd-C catalyst (having a Pd content of 5% by weight and a water content of 50% by weight), used in Example 1, the amount of 85% sodium hydroxide added was changed to 9.9 g, 19.8 g, 26.4 g or 33 g, whereby the 3,3', 4,4'-biphenyltetracarboxylic acid salt was synthesized. When the salt was converted to 3,3', 4,4'-biphenyltetracarboxylic acid for determining the yield, it was found that the yield was 13.0 g (94.4%), 12.8 g (93.0%), 12.5 g (90.8%) or 12.3 g (89.3%).

EXAMPLE 15

Sodium 3,3', 4,4'-biphenyltetracarboxylate was synthesized in the same manner as described in Example 1 except that 31.0 g of a white powder comprising 71.5 mole % of sodium 4-chloroorthophthalate, 3.8 mole % of sodium 3-chloroorthophthalate, 15.1 mole % of sodium orthophthalate and 9.6 mole % of sodium dichloroorthophthalate was used instead of the 4-bromoorthophthalate used in Example 1. For determining the yield, 3,3', 4,4'-biphenyltetracarboxylic acid was synthesized in the same manner as described in Example 1. It was found that the yield was 9.8 g (59.6%).

Comparative Example 1

A four-necked flask equipped with a thermometer, a reflux cooler and a stirrer and having a capacity of 300 ml was charged with 27.5 g of a light yellow powder comprising 80.9 mole % of sodium 4-bromoorthophthalate, 0.9 mole % of sodium 3-bromoorthophthalate and 18.2 mole % of sodium orthophthalate, 13.2 g of potassium hydroxide and 60 g of water, and an aqueous solution was formed. Then, 4.6 ml of methanol and 2 g of a metallic palladium-carbon catalyst (having a Pd content of 5% by weight and a water content of 50% by weight) were added to the solution. The 3,3', 4,4'-biphenyltetracarboxylic acid salt was synthesized in the same manner as in Example 1. For determining the yield, 3,3', 4,4'-biphenyltetracarboxylic acid was precipitated in the same manner as described in Example 1. The amount of the obtained acid was 8.3 g and the yield was as low as about 60.7%.

Comparative Example 2

The 3,3', 4,4'-biphenyltetracarboxylic acid salt was synthesized in the same manner as described in Comparative Example 1 except that 7.4 ml of butyl alcohol was used instead of methanol used in Comparative Example 1. For determining the yield, 3,3', 4,4'-biphenyltetracarboxylic acid was precipitated. The amount of the formed acid was 1 g and the yield was as low as about 7.2%.

As is apparent from the foregoing description, according to the process of the present invention for the preparation of a 3,3', 4,4'-biphenyltetracarboxylic acid salt, the intended product can be obtained in a high yield and can be recovered very easily. For example, the yield can be improved by about 25% over the yield attainable in the conventional process.

We claim:

1. A process for the preparation of a 3,3', 4,4'-biphenyltetracarboxylic acid salt by the dehalogenodimerization of a 4-halogenoorthophthalic acid salt, which comprises heating and reacting an alkaline aqueous solution containing, dissolved therein, a 4-halogenoorthophthalic acid salt and a base in the presence of (1) a catalyst comprising a noble metal supported on a carrier, a formic acid salt and a small amount of an aliphatic compound containing a hydroxyl group selected from the group consisting of methyl alcohol, ethyl alcohol, propyl alcohol, butyl alcohol, amyl alcohol, ethylene glycol, ethylene glycol monomethyl ether, and ethylene glycol monoethyl ether or (2) a catalyst comprising a noble metal supported on a carrier, which has been treated with the aliphatic compound containing a hydroxyl group in advance, and a formic acid salt.

2. A process for the preparation of a 3,3', 4,4'-biphenyltetracarboxylic acid salt according to claim 1, wherein the 4-halogenoorthophthalic acid is 4-bromoorthophthalic acid.

3. A process for the preparation of a 3,3', 4,4'-biphenyltetracarboxylic acid salt according to claim 1, wherein the base is an alkali metal hydroxide.

4. A process for the preparation of a 3,3', 4,4'-biphenyltetracarboxylic acid salt according to claim 1, wherein the catalyst comprising a noble metal supported on a carrier is a catalyst comprising metallic palladium supported on a carrier.

* * * * *